(12) United States Patent
Maynard

(10) Patent No.: US 6,720,313 B1
(45) Date of Patent: Apr. 13, 2004

(54) BIOCIDAL COMPOSITION CONTAINING PHOSPHITE IONS

(75) Inventor: Nigel Paul Maynard, Auckland (NZ)

(73) Assignee: Mattersmiths Holdings Limited, Auckland (NZ)

(*) Notice: Subject to any disclaimer, the term of this patent is extended or adjusted under 35 U.S.C. 154(b) by 5 days.

(21) Appl. No.: 09/688,693

(22) Filed: Oct. 17, 2000

Related U.S. Application Data

(63) Continuation of application No. PCT/NZ99/00045, filed on Apr. 13, 1999.

(30) Foreign Application Priority Data

Apr. 17, 1998 (NZ) ................................. 330219
Jul. 14, 1998 (NZ) ................................. 330982

(51) Int. Cl.$^7$ ..................... A61K 31/66; A61K 31/535; A61K 31/41; A01N 43/42; A01N 43/64; A01N 43/52
(52) U.S. Cl. ..................... 514/75; 514/231.2; 514/299; 514/307; 514/383; 514/394
(58) Field of Search ................ 514/186, 75, 299, 514/307, 231.2, 394, 383

(56) References Cited

U.S. PATENT DOCUMENTS

| | | |
|---|---|---|
| 1,571,814 A | 2/1926 | Stewart |
| 4,075,324 A | 2/1978 | Thizy et al. |
| 4,119,724 A | 10/1978 | Thizy et al. |
| 4,139,616 A | 2/1979 | Duncret et al. |
| 4,188,380 A | 2/1980 | Oswald |
| 4,950,685 A | 8/1990 | Ward |
| 5,324,967 A | 6/1994 | Honma et al. |

FOREIGN PATENT DOCUMENTS

| | | | |
|---|---|---|---|
| AU | A24347/88 | * | 4/1989 |
| AU | A-24347/88 | | 4/1989 |
| EP | 0 355 383 A1 | | 2/1990 |
| EP | 0-648-416 A1 | | 4/1995 |
| JP | 85016401 | * | 12/1979 |
| JP | 223719 | * | 5/1987 |
| JP | 62099309 | * | 5/1987 |
| NZ | 225428 | | 3/1991 |
| NZ | 233846 | | 4/1992 |
| NZ | 260826 | * | 2/1996 |
| NZ | 264671 | | 3/1996 |
| NZ | 260462 | | 4/1996 |
| WO | WO 95/30332 | | 11/1995 |

OTHER PUBLICATIONS

Arthur I. Vogel, Quantitative Inorganic Analysis, 1966, p. 387, Third Edition, Volumetric (Titrimetric) Analysis.
Derwent Abstract Accession No. 66832 D/37, JP 56092802 A (Mitsugishi Chem Ind KK) Jul. 27, 1981, Abstract.
Derwent Abstract Pub. No.: EP 223719A Synergistic Fungicide Contg. Pyroxfur and Phosphorus Acid deriv.–esp. Aluminum Tri:ethyl Phosphite for Broad Spectrum Control of Soil Borne Fungi May 27, 1987, Abstract.
D. R. Stojakovic, A Study of the Acidity of Aqueous Phosphorous and Phosphoric Acid, Aug. 7, 1996, vol. 70, pp. 1419–1424, Polish J. Chem.
The British Crop. Protection Council, The Pesticides Manual, 1979, p. 80.

* cited by examiner

*Primary Examiner*—Alton N. Pryor
(74) *Attorney, Agent, or Firm*—Jacobson Holman PLLC

(57) ABSTRACT

A biocidal composition useful for providing antifungal or antibacterial protection to a substrate such as wood, the composition comprises in its use form a use solution of pH of 4 or below containing at least one biocide and a source of free phosphite ions.

A preferred source of phosphite ions is phosphorous acid.

The composition allows deep penetration of a biocide such as copper oxine into where it can be fixed by pH change and confer a degree of protection beyond that hitherto obtained with such a biocide simply applied to the surface of the substrate.

41 Claims, 1 Drawing Sheet

BIOCIDAL COMPOSITION CONTAINING PHOSPHITE IONS

This is a Continuation of PCT International Application No. PCT/NZ99/00045, filed Apr. 13, 1999.

TECHNICAL FIELD

This invention relates to fungicides and is intended particularly to provide a fungicidal composition and/or a method of preparing a fungicidal composition, particularly but not exclusively for application to lignocellulosic substrates so as to confer an antifungal characteristic to logs, lumber or other products derived from said lignocellulosic substrates and to other organic substrates such as leather products and paint.

BACKGROUND ART

Whilst still alive and growing, trees, suitable for conversion to lumber or other lignocellulosic products, are relatively immune from or are self protecting against fungal attack. After felling logs are immediately vulnerable to attack due to cutting or bark damage due to colonisation by fungi. Damage to the substrate initially appears as visual degrade (due to pigment formation by the fungi) which lowers the value of the substrate but later this may also lead to physical degrade which may negate the value of the substrate. To protect these or products derived from them from degradation it is common practice to treat these with aqueous fluids containing fungicides (biocides).

Historically a wide range of fungicides has been used including toxic substances such as sodium pentachlorophenate, trichlorophenol, and mercury compounds. Modern prophylactic formulations generally use less toxic compounds although those more toxic are still used in some cases. Often when cost is a major consideration, and more so in less developed countries, more hazardous compounds continue to be used. Where cost is an issue, a more competitive formulation will offer a viable option.

More recently the lumber industry has been looking closely at prophylactic formulations to further reduce any potential threat and in doing so has been scrutinising formulating aids typically used in these formulations. Some concern is evident regarding certain solvents, and other additives have been recognised as posing a threat to workers using these products.

Traditionally prophylactic treatment formulations have been formulated such that they, by design or default, adhere to, fix to or precipitate at the surface of the substrate.

For example, one of the earlier biocides used, pentachlorophenol was formulated at a high pH, as the sodium salt of the otherwise relatively insoluble pentachlorophenol. Upon application to the substrate as an aqueous solution the pentachlorophenol would precipitate due to the buffering action of the wood which has a natural pH of approximately 4.0. Although highly toxic, pentachlorophenol did have an advantage over most modern biocides in that it has a high vapour pressure so was able control fungal degrade remote from the point of application by fumigant action.

U.S. Pat. No. 4,950,685 to Kop-Coat teaches the formulation of a synergistic prophylactic formulation comprising dodecyl dimethyl ammonium chloride (DDAC) and iodo propynyl butyl carbamate (IPBC) as co-biocides. In this case, for example, when applied to wood, DDAC will fix to the wood surface by an ion exchange mechanism and since the DDAC, which acts as a surfactant solubiliser for the IPBC, has been deactivated by binding to the substrate, the IPBC, which has low solubility in water, precipitates at the surface also.

U.S. Pat. No. 1,571,814 to Chapman Chemical teaches the solubilisation of copper 8-hydroxyquinolinolate using various strong organic acids. The biocides of this invention have good efficacy and are relatively inexpensive. The acids used however are corrosive to metals that may be involved in the containment of the formulations during use, add significantly to cost, cause foaming (which is inconvenient and potentially hazardous) and may be toxic to workers exposed to the product. The mechanism of fixation in this instance also relies on the natural buffering pH of the substrate (4.0) wherein the treating solution with a pH normally around 2.5 to 3 will precipitate the copper 8-hydroxyquinolinolate when the pH increases to 4.0 on the substrate surface. It has been well documented that copper 8-hydroxyquinolinolate completely precipitates when the pH is greater than 3.3 (Arthur I. Vogel. A Text-book of Quantitative Inorganic Analysis, Third edition 1966 Longmans).

Similarly NZ Patent 225428 to Chemicca describes an organic solvent based formulation combining copper 8-hydroxyquinolinolate (frequently referred to in the art as "oxine copper") and carbendazim (methyl benzirnidazoyl carbamate) using dodecyl benzene sulphonic acid as a solubilising agent. The principle of solubilisation and precipitation of this formulation is the same as that of U.S. Pat. No. 1,571,814 except that carbendazim requires higher levels of acid to solubilise the additional biocide. This leads to an additional disadvantage for this type of formulation in that it is more expensive and in that the carbendazim precipitates more readily. This occurs where contamination of the treating solution occurs with natural salts from the source of water, or chemicals from the wood itself leach into the treating solution, raising the pH to a point where the carbendazim begins to precipitate prematurely. This leads to agglomeration of carbendazim particles and, and eventually to changes in the rheology of the solution making the product difficult to use and in some cases, for example, when it may be sprayed, impractical to use. The formulating aids used in this type of formulation are costly and also impose an additional biological load on the environment. Foaming of the product in use is frequently a problem.

Many other products have been produced for this market including suspension concentrates or flowables wherein the insoluble biocides are ground to a very small particle size (less than 10 microns) and then stabilised in suspension using various aids. These formulations are expensive to produce but more significantly precipitate during use necessitating continuous vigorous agitation, and are precipitated at the wood surface by a filtering action.

It is now being more widely recognised that certain fungal species, which colonise wood and derivatives, grow remarkably rapidly (for example many of the Ophiostoma species) and can penetrate into the substrate from the surface at an easily detectable rate. Wood and many other natural products are very rarely treated with prophylactic materials at the time of initial production and therefore may be well colonised by degrading organisms before any biocide is applied. It is therefore logical that these organisms may be well out of reach of, and therefore are unable to be controlled by, any biocide that precipitates or remains very close to the surface of the substrate. This is now well recognised by those working in the industry. Historically pentachlorophenol and trichlorophenol were able to achieve a level of control by the fumigant action previously mentioned.

Unfortunately pentachlorophenol and trichlorophenol have generally been prohibited from use due to its high toxicity. Few other fungicides have a similar action and those that do are also acutely toxic such as methylene bis-thiocyanate.

There is a need therefore for a prophylactic treatment system that allows the biocide or biocides to penetrate further into the substrate prior to precipitation. Very strong acids can be used to dissolve many of these biocides but they are hazardous, can destroy the wood substrate and will certainly aggravate any corrosivity.

Although preferred fungicidal actives are now being chosen from a group having very low toxicity, other components still pose problems. These include those used in the aforementioned patents and can be summarised to include;

high toxicity to users (by ingestion, skin contact or inhalation)

high levels of irritation strong offensive odour corrosivity to metals high levels of foam formation poor physical properties leading to improper application such as:

high viscosity precipitation and agglomeration of actives a poor rheology leading to poor spraying loss of actives during recovery and recycle.

Formulating aids that have been used to solubilise biocides include toluene sulphonic acid, benzene sulphonic acid, dodecylbenzene sulphonic acid, and lactic acid, amongst others. Typically dodecylbenzene sulphonic acid (DDBSA) has been used which has the disadvantage of being quite toxic, irritant, corrosive to metals, causes foam formation and which poses a biological load to the environment.

Whilst solubility of biocides at high concentrations in aqueous systems and stability at such concentrations is important in the preparation of stable formulations for temporary protection of wood or other substrates, the low final use rate concentrations can tolerate higher manufacturing and distribution costs.

It is more critical in the preparation of biocide formulations for permanent preservation of lumber that all costs be minimised because quite high loadings of biocides are impregnated into the lumber.

For example, two proven preservatives for the permanent preservation of wood include Copper Chrome Arsenate (CCA) and oxine copper.

CCA is prepared by dissolution in water of a mixture of copper, chromium and arsenic compounds. These typically include cupric oxide, chromium trioxide and arsenic pentoxide. This mixture is clearly highly toxic. The formulation is shipped at a concentration of approximately 60 per cent to minimise the impact of the freight cost on the final delivered price. Whilst this type of preservative is highly toxic it can be shipped in high volumes to remote treatment plant sites competitively.

CCA is an extremely effective permanent preservative for lumber and can be produced cost effectively. The major disadvantages of CCA are;

toxic and hazardous to produce hazardous to use long term environmental impact of waste when treated lumber is retired from service Oxine copper is a biocide with low toxicity (cf Oral $LD_{50}$ Rat 10,000 mg/kg versus arsenic $LD_{50}$ Rat 15–293 mg/kg and which is also carcinogenic).

Oxine copper has until this invention was developed been formulated in two principal ways.

(A) solubilised in complex solvent systems with metal soaps such as Nickel Hexanoate added as solubilising agents. (The concentration of oxine copper is generally 10 per cent or below because this is near the limit of solubility. Consequently the formulation is expensive to formulate, freight and use. This restricts commercial acceptability to use for treatment of lumber for more critical areas such as food contact use or playground equipment for children), (B) solubilised in dodecylbenzene sulphonic acid with a co-solvent such as propanol or ethylene glycol. (The concentration of oxine copper is 10 per cent or below because this again is near the limit of solubility. Also, at this concentration the product becomes very viscous and difficult to handle. The high level of formulating aids required to achieve this concentration makes this product uncompetitive for permanent preservation of lumber).

We have carried out many solubility studies using the technology of this invention. For example, we are able to produce solutions stable at ambient temperature of oxine copper at concentrations greater than 100 grams per 200 mls of final product. Because the specific gravity of such solutions is approximately 2.8 this yields a solution of oxine copper of 50 per cent weight/volume or more. This concentration is commercially viable to use and eliminates many of the potentially toxic or flammable formulation aids used in prior art solubilisation of oxine copper.

Oxine copper is approved for use in permanent preservation of lumber (US AWPA P8-95) at 0.02 pounds per cubic foot (0.32 kilograms per cubic metre) compared to CCA at 0.25 pounds per cubic foot (4.00 kilograms per cubic metre) for a similar end use. Because the use rate for this biocide in permanent preservation of wood is lower than CCA and because we can produce stable highly concentrated solutions we can minimise the impact of manufacturing, packaging and freight costs on the delivered price. This is anticipated to enable the competitive use of oxine copper (a low toxicity biocide) in situations where otherwise highly toxic CCA would be used. Further benefits accrue from the use of the technology of this invention. Since the required retention of biocide is significantly lower than CCA the total mass of biocide used by industry may be decreased by an order of magnitude. Not only is this essential and beneficial during use of the biocide, it is also significantly more important when the lumber is retired from service in which case oxine copper treated lumber exposes very low levels of heavy metals to the environment compared to CCA which will release copper, chromium and arsenic in large amounts.

It is important also that the preservative be a stable solution in both concentrated form and when diluted for application such that the end use solutions can be reused if surplus during a treatment process or may have further water and biocide concentrate added for make up and reuse. This invention because of the specific acid used and the high solubility and stability of the resultant solutions is able to achieve this requirement previously unachievable.

DISCLOSURE OF THE INVENTION

The present invention relates to fungicides and is intended particularly to provide a fungicidal composition and/or a method of preparing a fungicidal composition, for application to lignocellulosic or proteinaceous substrates so as to confer an antifungal characteristic to logs, lumber or other products derived from said lignocellulosic substrates or hides or leather substrates, wherein preferably the biocides are truly solubilised and maintained at a pH which provides stability as a concentrate and also as a working solution and also where said formulation offers additional mobility to said biocides such that they may be active at a point remote from that of application.

In a first aspect the invention is a biocidal composition being in the form of
(1) a solution carried by a liquid selected from the group consisting of water and polar solvents, or
(ii) as a solids mix soluble in a liquid solvent selected from the group comprising water and polar solvents,
said composition having
a source of free phosphite ions selected from the group comprising phosphorous acid and phosphite compounds capable of releasing phosphite ions at a pH of below 4 and at the pH of the true solution hereinafter referred to, and
at least one biocide,
wherein, as a true solution in the presence of said liquid, the pH is or will be below 4.

Preferably said composition is an antifungal composition and/or an antibacterial composition.

Preferably water is present.

Preferably said liquid is at least primarily water.

Preferably said liquid is water.

Preferably phosphorous acid is the source of the phosphate ions.

Phosphorous acid is the preferred acid because it is a very strong acid (stronger than phosphoric acid), it has biocidal properties and in some instances it is synergistic with biocides of this invention.

Use of phosphoric acid is not preferred because it produces inferior biological performance, an unstable composition and makes no biocidal contribution.

The solvent (ie; the liquid) is preferably water for reasons of cost and flammability but could include lower alcohols (methanol, ethanol or propanol), or other solvents such as glycols, glycol ethers, glycol esters, cyclic lactams or cyclic lactones, ketones and others and mixtures thereof.

Preferably said at least one biocide is stable at a pH below 4 or said biocide or biocide precursors form or become stable biocide(s) as the pH of the use strength solution rises to a pH of 4.

Preferably the pH is or will be below 3.

Preferably the pH is or will be below 2.5.

Preferably said at least one biocide is selected from the group comprising benzimidazoles, precursors of benzimidazoles, substituted morpholines, organic chelate complexes of metals, precursors of such organic complexes of metals, metal ions selected from the group consisting of Al, Co, Cu, Mn, No, Ni, Wo, Va and Zn.

Preferably a benzimidazole is present.

Preferably said biocide is a said organic chelate complex of a metal.

Preferably said organic chelate complex is of an 8-hydroxyquinoline.

Preferably the metal is copper or zinc and the complex is an oxine of copper or zinc cations with 8-hydroxyquinoline.

Preferably said cations are of copper (ie; copper oxine).

Preferably phosphorous acid and/or any other source of phosphite ions is or are in a stoichiometric relationship to the biocide(s) to the extent required to ensure at least substantially fill solubility of the biocide(s) in said liquid.

Preferably phosphite ions are present and the hydrogen ion concentration from the source of phosphite ions or other acid contribute to a pH below 4.

Preferably phosphorous acid is or has been present and is in a stoichiometric relationship to copper oxine such that at least substantially all of the copper oxine is in solution.

Preferably phosphite ions are present and the hydrogen ion concentration from the source of phosphite ions or other acid contribute to a pH below 4.

In another aspect the present invention consists in an antifungal composition in the form of a solution comprising
oxine copper (ie; a copper cation complex with 8-hydroxyquinoline), phosphorous acid, and
water, the pH being less than 4.

Preferably the pH is less than 3.

Preferably the pH is about 2.5 or less.

Preferably another biocide is present in solution.

Preferably as a wood preservative wherein, in time, at the pH of wood, said at least one biocide will fix in the wood from the lower pH solution.

Preferably the biocidal composition contains a stable highly concentrated solution of biocidal.

Preferably the biocide is a metal chelate of the precursors thereof Preferably the metal chelate is a metal chelate of oxine (8-hydroxyquinoline) or a mixed chelate thereof or the precursors thereof; more preferably the metal chelate is oxine copper or the precursors thereof.

In still another aspect the invention consists in an antifungal composition comprising or including;
phosphorous acid, and
at least one acid stable biocide selected from the group comprising
benzimidazoles which are stable in acid conditions,
precursors of benzimidazoles,
substituted morpholines which are stable in acid conditions,
organic chelate complexes of metals, and
precursors of such organic chelate complexes of metals, and water and/or other polar solvent(s).

Where phosphorous acid is used to solubilise acid stable biocides to produce formulations (preferably which contain a stoicheiometric excess of phosphorous acid;) active ingredient concentrations of greater than 5 per cent biocide by weight and phosphorous acid preferably greater than 5 per cent by weight (more preferably greater than 10 per cent biocide by weight) are used.

Active ingredients include but are not restricted to; metal chelates or one or more precursors thereof, Fenpropimorph and other substituted morpholine fungicides, Carbendazim and other benzimidazoles, metal phosphites and/or metal ions including but not restricted to those of copper, zinc and aluminium and/or other acid stable fungicides.

In another aspect the present invention consists in an antifungal composition at least having an acid stable biocide (s) solubilised in a liquid system at a pH below 4.0 such that, upon delivery into a matrix, for example wood or leather, rising pH conditions over time will lead to the fixing of the acid stable biocide(s).

Preferably acid stable biocide(s) or biocide or biocide precursors which form or become stable biocide(s) as the pH of the use strength solution rises to a pH of 4, said composition being subjected to treatment with a pH increasing solution to facilitate fixing of the biocide(s).

Preferably said pH increasing solution contains further biocide(s).

Optionally present is a latent buffer which will raise the pH of the solution over time to facilitate fixing of the biocide(s).

Preferably the composition is applied to a substrate where a latent buffer will raise the pH of the solution over time to facilitate fixing of the biocide(s).

Preferably the acid stable biocide(s) or biocide or biocide precursors which form or become stable biocide(s) as the pH of the use strength solution rises to a pH of 4 is supported in phosphorous acid which optionally may include water and/or other polar solvent(s).

In another aspect the invention consists in an antifungal and/or antibacterial composition which is a true solution (or soluble concentrate) comprising or including;

at least one biocide selected from the group comprising benzimidazoles, precursors of benzimidazoles, substituted morpholines, organic chelate complexes of metals, precursors of such organic complexes of metals, metal ions (Al, Co, Cu, Mn, Mo, Ni, Wo, Va and Zn), and other acid stable fungicides, free or mobile phosphite ions (ie; phosphite ions in solution, not as undissolved metal or organic phosphates) and, water and/or other polar liquid miscible with water, and wherein the composition has or, in the presence of water, will have a pH less than 4.0

Preferably phosphite ions have been provided by phosphorous acid.

Preferably phosphite ions are sourced from the addition of a strong acid to a phosphite salt.

Preferably sufficient hydrogen ions are present to ensure the pH of the solution is below 4.

Preferably the phosphorous acid is in stoichiometric excess of the biocide(s).

In another aspect the invention is a method of forming a biocidal composition (i) being in or to be in the form of a solution carried by a liquid selected from the group consisting of water and polar solvents or (ii) as a solids mix soluble in a liquid solvent selected from the group comprising water and polar solvents, said composition having a source of free phosphite ions selected from the group comprising phosphorous acid and phosphite compounds capable of releasing phosphite ions at a pH of below 4 and at the pH of the true solution hereinafter referred to, and at least one biocide, wherein, as a true solution in the presence of said liquid, the pH is below 4, said method comprising any one of the following

(20) admixture of the individual composition components and mixing to provide dissolution to produce the solution,

(21) addition of biocide precursors as in (a) with remaining composition components to form the solution,

(22) admixture for components prior to addition of water or polar solvent with subsequent addition of water or polar solvent to form the solution.

(23) addition of biocide precursors as in (b) with remaining components prior to addition of water or polar solvent with subsequent addition of water or polar solvent to fore the solution,

(24) admixture of the individual composition components and mixing to form the solution with subsequent addition of further biocide components, and

(25) admixture of the individual composition components with subsequent addition of a source of hydrogen ions to reduce the pH of the composition to below 4 to form the solution.

In another aspect the invention consists in a method of treating a substrate which comprises applying to such substrate an effective amount of a biocidal composition as previously defined.

Preferably said substrate has a pH above that of said u solution in the presence of said liquid.

Preferably said substrate is wood.

In still a further aspect the present invention consists in the use of a (phytotoxic) antifungal composition in accordance with the present invention, in particular a method of use of such composition wherein;

the composition is applied to a substrate (eg: by dipping the substrate in the composition or a solution of the composition, spraying the substrate with the composition or a solution of the composition, brushing the substrate with the composition or a solution of the composition, and/or treating the substrate with any variation of vacuum and/or pressure cycles applied to the substrate surrounded by the composition or a solution of the composition)

and whereupon, subsequent to the application of the composition, the biocide is allowed to precipitate on or in the substrate due to an increase of pH provided by chemical action on or within the substrate.

Since the composition is usually phytotoxic because of the low pH it should be applied preferably to substrates which do not suffer from such phytotoxicity. This precludes application to living plants.

The preferred substrate to be treated is a substrate which may suffer from visual or physical degrade by organisms namely fungi or bacteria and could include wood, concrete, leather, painted surfaces or any other solid substrate and may include liquid for example, water in cooling towers wherein subsequent to application the biocide is immobilised by precipitation caused by an increase in pH and wherein such pH is caused by alkalinity of the substrate or by a pH buffering action of the substrate.

The preferred substrate is a lignocellulosic material which can include wood, composite board, chips or fibre or animal hides (including leather).

The most preferred substrate is freshly felled and debarked logs and freshly sawn lumber.

DETAILED DESCRIPTION OF THE INVENTION

Figure 1:
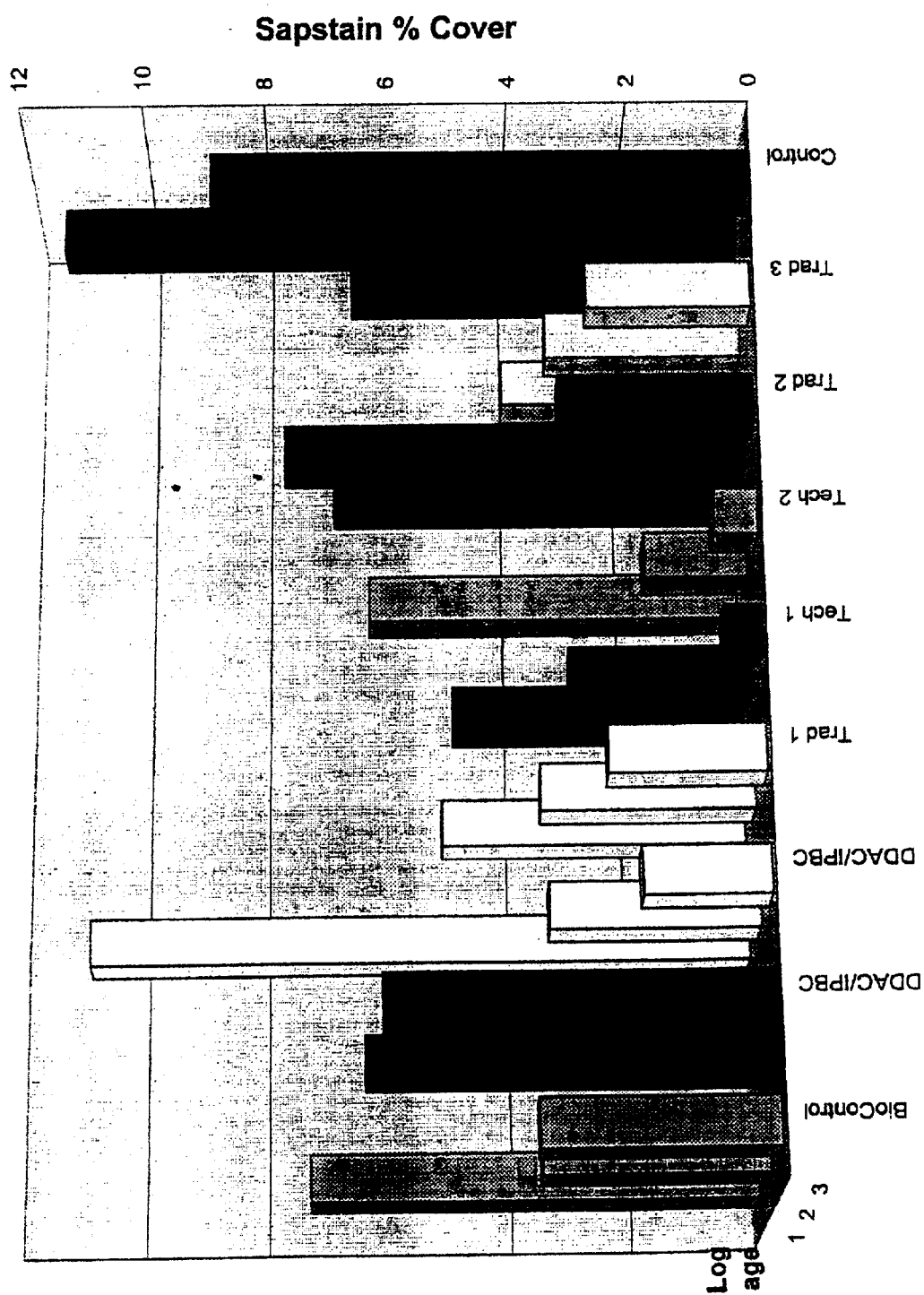
FIG. 1: Comparison of Biocide Compositions

Preferred forms of the present invention will now be described hereafter.

Prophylactic Laments for lignocellulosic or proteinaceous substrate normally comprise three different formulation types;

emulsions of organic biocides suspensions of organic or inorganic biocides solutions of organic biocides A disadvantage of emulsion and suspension fungicide formulations is that the solution prepared therefrom for treating the substrate becomes non-homogeneous over time, that is the fluids may stratify due to the dissimilar nature of the two phases. This is particularly so where suspensions frequently precipitate active ingredient. A further disadvantage is that many emulsions and the majority of suspensions remain at the surface of the substrate giving reduced efficacy within the substrate. Such biocides also require addition of non-biocidal additives to facilitate manufacture of the composition. These can be expensive and can often be toxic.

Our work has demonstrated that true solutions of biocides offer many advantages over emulsions and suspensions, particularly when combined with the dissolution technique of this invention.

These advantages include:

the biocides remain in solution and are therefore uniformly distributed throughout the fluid;

the formulation provides greater efficacy due to more uniform distribution on the treated substrate:

the treating solution is less likely to become unstable in the presence of extraneous compounds which might otherwise destabilise less robust formulations;

the treatment solution is significantly less likely to become non-homogeneous;

manipulation of pH of these true solutions enables a level of control of penetration of the biocides into the substrate;

manipulation of pH of these true solutions enables a level of control of the rate of fixation or precipitation of the biocides from solution in or on the substrate;

true solutions provide better penetration into the substrate. (This is more desirable than for example suspensions which are filtered out at the surface by the morphology of the substrate).

We have determined the desirability of maintaining biocide solutions of those biocides which are insoluble or of low solubility at pH greater than 4, below a pH of about 4.0 since this is the natural pH of wood and the logically point where such biocides would otherwise begin precipitating.

Our research has clearly identified areas where specific attention must be given to the combination of phosphorous acid and biocides.

For example, when the organic chelate complex formed between copper and 8-hydroxyquinoline is used in a prophylactic formulation for the protection of lumber, in the presence of iron compounds that are frequently encountered in feed water, the copper chelate becomes unstable and the copper is displaced from the chelate by the iron. For example at pH 2.8 the iron chelate has lower solubility than the copper chelate and therefore precipitates from solution. This results in a black precipitate that can disfigure the treated substrate. Since the iron chelate has a significantly lower bio-efficacy this process also reduces the bio-efficacy of the formulation by removal of an active component from the solution. It has been found that in the present invention the high level of phosphorous acid can alleviate this problem of precipitation by maintaining pH at a point where the iron chelate remains soluble.

Similarly transition metal chelates in their own right may impart colour to the surface of a substrate such as wood and at certain times this may not be desired by the user. This may sometimes be the case with for example oxine copper, which is known to produce a strong red brown colouration on the wood surface by what is believed to be a photochemical reaction in association with wood extractives. It is proposed in this invention that this discolouration will be minimised by the biocide migrating further into the substrate prior to fixation due to the solubilising technique used, subsequent to which the biocide fixes within the substrate. This will minimise discolouration whilst providing more permanent fixation. This in turn provides higher efficacy due to lower photochemical reaction and a reduction of elution of the biocide into the environment, by for example rain, because of the incorporation within the substrate.

The relative solubility of 8-hydroxyquinoline chelates is reported in A Textbook of Quantitative Inorganic Analysis Vogel A.I., 3$^{rd}$ Edition 1961, Longmans, Green and Co. Table 1 demonstrates the relationship between pH and the solubility of chelates of oxine (8-hydroxyquinoline) of and various metals.

TABLE 1 pH range for precipitation of metal oxinates.

| Metal | pH initial precipitation | pH complete precipitation |
| --- | --- | --- |
| Aluminium | 2.9 | 4.7–9.8 |
| Bismuth | 3.7 | 5.2–9.4 |
| Cadmium | 4.5 | 5.5–13.2 |
| Calcium | 6.8 | 9.2–12.7 |
| Cobalt | 3.6 | 4.9–11.6 |
| Copper | 3.0 | >3.3 |
| Iron | 2.5 | 4.1–11.2 |
| Lead | 4.8 | 8.4–12.3 |
| Magnesium | 7.0 | >8.7 |
| Manganese | 4.3 | 5.9–9.5 |
| Molybdenum | 2.0 | 3.6–7.3 |
| Nickel | 3.5 | 4.6–10.0 |
| Thorium | 3.9 | 4.4–8.8 |
| Titanium | 3.6 | 4.8–8.6 |
| Tungsten | 3.5 | 5.0–5.7 |
| Uranium | 3.7 | 4.9–9.3 |
| Vanadium | 1.4 | 2.7–6.1 |
| Zinc | 3.3 | >4.4 |

The chelates of this invention include but are not restricted to fungicidal cations such as copper and zinc. Table 1 demonstrates that to maintain solubility for these metal complexes or complex precursors the solution pH must be maintained below 3.3 for zinc and below 3.0 for copper. This is adequate when working with pure water. However since water is frequently contaminated at trace levels with iron and manganese whose chelates form disadvantageously coloured compounds, it is preferable to maintain the pH below 2.5. It can be seen that selection of this pH will prevent precipitation of all but the chelates of vanadium and molybdenum, which fortunately for the user are uncommon in feed water.

It is therefore an object of this invention to have an acid solution of biocide preferably below the natural pH of lignocellulosic materials such as wood and more preferably below a pH where metal complexes might precipitate. The preferred pH is below 4.0, more preferably below 3.0 and most preferably below 2,5.

U.S. Pat. No. 4,119,724 and U.S. Pat. No. 4,139,616 describe the use of salts of phosphorous acid as fungicides. These are prepared by addition of stoicheiometric quantities of precursors of the compounds concerned to produce the salt desired. We have produced similar compounds by the methods taught in this art. Our work has demonstrated that for typical transition metals (copper, iron, nickel, cobalt and manganese) these compounds have negligible solubility at neutral pH and particularly at the pH used in the aforementioned prior art where the claimed transitional metal phosphites are clearly claimed to be neutral salts. Whilst the compounds produced by this art may be effective as biocides, being insoluble, it is most likely they will need to be formulated as suspensions due to their insolubility in water. It is believed these biocides in the form claimed will not have the benefits of the present invention because they are particulate and therefore suspensions will likely stratify and fluids containing them will not penetrate into the substrate for reasons previously stated.

Since our objective is to produce truly soluble formulations and more so with commercially acceptable concentrations of biocides, we decreased the pH to a point where these compounds once again become soluble. For example, the following table describes the solubility of certain metal phosphorous acid salts with respect to pH.

TABLE 2

Solubility of transition metal phosphites versus pH.

| Cation | pH = 7 | pH for dissolution |
|---|---|---|
| copper | Insoluble | <3.5 |
| iron | Insoluble | <3.5 |
| manganese | Insoluble | <4.5 |
| cobalt | Insoluble | <4.5 |
| nickel | Insoluble | <4.5 |

We believe we can provide a formulation that remains stable when certain salts and compounds may elute into the solution from the substrate or arise from the source of water or solvent used to dilute the formulation. We have demonstrated that a high level of phosphorous acid anions and low pH is essential to the formulation.

We believe also that phosphite salts of metals can be incorporated as biocides (eg: in the specific circumstances of the invention) where they have been solubilised in excess phosphorous acid and wherein the pH is below 3.5. Those versed in the art will be aware that this may also be achieved by use of alternative methods of pH reduction. For example by addition of phosphite ions where pH is adjusted with an alternative source of hydrogen ions such as a secondary acid and this is hereby also claimed.

We further explored the requirements of incorporating organic biocides. We had previously reviewed the art of PCT/NZ95/00029 wherein a triazole fungicide is included with a phosphite salt. The New Zealand licensee confirmed that Foli-R-Phos, the wed source of phosphite ions said patent, is in fact a mixed salt of mono potassium and di potassium phosphite. Of necessity this formulation or others including this product, must have a pH greater than 6 preferably between 6 and 7 otherwise the crop to which it is applied will be destroyed. Similarly it can be demonstrated from theoretical grounds, that a composition of mono potassium and di-potassium phosphites will have a relatively high pH, closer to neutral, rather than the pH we require in products of this invention. Vogel teaches the first equivalence point for a polybasic acid is pH=(½pK1+½pK2). Since phosphorous acid has pK1=1.8 and pK2=6.15 we can calculate the first point being approximately equal to pH=4. The second equivalence point for this acid is pH=½pKw+½pK2+½logc where pKw is the dissociation constant for water and c is the concentration of acid. Calculating the pH for strong acid solutions such as those of this invention shows the second equivalence point will be greater than pH=10. Since Foli-R-Phos is an equal mixture of mono and di phosphite salts the pH will be an average of these that is at least pH=7. Even for higher proportions of the monobasic salt the pH will be greater than 4 and therefore fall outside the claims of this invention.

It is also known that strong inorganic acids, which includes sulphuric acid, are destructive of living plants and may be used as herbicides (The Pesticides Manual 1979. 6$^{th}$ Edition. The British Crop Protection Council). This is attributed to the high acidity and low pH. Since it is well known that the salts of these acids (phosphates, phosphites and sulphates) are effective fertilisers and beneficial to living plants under neutral conditions the pH must lie between 6.0 and 7.5.

We also wished to include other acid stable biocides that may include but is not be restricted to Fenpropimorph or other substituted morpholines and Carbendazim or other substituted benzimidazoles. Our work has demonstrated that to obtain a true solution it is required that the pH be below 4.0. For example, Fenpropimorph forms insoluble globules or micelles in the aqueous phase when the pH is above 4.0 not a true solution as is required.

The requirement to reduce the pH to below 4.0 and the requirements for solubilisation of transition metal phosphites and/or chelates reinforces the need to achieve the additional requirement of a composition having a pH of below 4.0, the natural pH of the lignocellulosic substrate. Subsequent to application the buffering action and the natural pH of the substrate will encourage precipitation on or within the substrate such that the biocide will reside on or within the substrate for a period sufficient to meet the user's expectations of performance.

It has been reported previously that organic biocides such as Carbendazim produce biologically active salts with inorganic acids. When used for protection of plants these formulations must have relatively neutral pH for the reasons previously given. The Pesticides Manual states use of Hydrochloride salts to control elm disease. Salts generally have a pH closer to neutral depending on the relative strength of the acid and base used, and therefore fall outside the claims of this invention.

It is less commonly known that phosphorous acid has substantially greater acidity than a similar acid phosphoric acid. Vogel reports pK1 for phosphoric acid to be 2.12 and that for phosphorous acid to be 1.8, which being relatively similar does not explain the greater acidity. Researchers in Poland have reported (Stojakovic D. R., *Polish Journal of Chemistry*. 70(11): 1419–1424, 1996 Nov.) that this effect is due to the greater hydration energy of the $H_2PO_3$ anion relative to that of the $H_2PO_4$ ion. Such an effect is caused by a higher partial negative charge on two of the oxygen atoms in phosphorous acid than in phosphoric acid. We believe this contributes to the higher concentration and stability of phosphorous acid solutions of acid stable biocides.

For example, in our original work we compared solutions of biocide in phosphoric acid with those in phosphorous acid. We found that the biocides in phosphoric acid were not stable and precipitated crystals of biocide phosphate salt, this occurring at ambient temperature. Those produced at equivalent biocide concentration with phosphorous acid remained stable and did not precipitate salts even when the solutions were cooled to minus 4 Celsius. Table 3 demonstrates the benefit of using phosphorous acid over phosphoric acid.

TABLE 3

Stability of phosphorous acid solutions of biocides

| | Composition % w/w | | | | | |
|---|---|---|---|---|---|---|
| Example | Phosphorous acid | Phosphoric acid | Copper oxinate | Carbendazim | Propiconazole | Stability |
| 1A | 60 | | 5 | 5 | | stable |
| 2A | | 60 | 5 | 5 | | precipitates |
| 3A | 60 | | 5 | 5 | 2 | stable |
| 4A | | 60 | 5 | 5 | 2 | precipitates |
| 5A | 60 | | 5 | | 2 | stable |
| 6A | | 60 | 5 | | 2 | precipitates |

When manufacturing formulations of biocides for the prophylactic treatment of lumber it is important to prepare products with the highest concentration of active ingredient as possible. This helps minimise the impact of the additive costs of manufacture, packaging, labelling and shipping which can have a significant negative impact on cost effectiveness. This is particularly important when competing in cost driven markets where toxic Sodium pentachlorophenate is still used. To use normal mineral acids is not practical because corrosiveness becomes a serious issue and more significantly for example when using phosphoric acid high concentrations of biocide in solution can not be achieved because crystallisation and precipitation occurs. This dictates that only dilute solutions can be shipped and this is impractical for cost reasons. Use of phosphorous acid has suprisingly yielded very concentrated and very cost competitive products to provide the user with a practical alternative to Sodium pentachlorophenate.

We also wished to provide the user an alternative, which might ameliorate environmental contamination, for example, where subsequent to application there might be a possibility of egress of biocide into the environment. This might for example be due to wash off by rain falling immediately on the treated substrate prior to any opportunity for penetration of the biocide into the substrate and/or any fixation of the biocide in the substrate due to buffering or raising of pH by the substrate.

We carried out several studies, some in aqueous systems and others on wood subsequent to the biocide formulation being applied, wherein we applied a further solution with higher pH to increase the pH to greater than 5. In aqueous solutions of biocides of this invention, addition of a solution of higher pH caused immediate precipitation of solubilised oxine copper, transition metal phosphites, and organic biocides such as Carbendazim and Fenpropimorph. This was immediately apparent visually. This confirmed the low solubility of the biocides at more neutral pH as reported in the literature.

Similarly when we applied the higher pH solution to wood which had immediately previously been treated with solubilised oxine copper we noted a precipitation of oxine copper at the wood surface was clearly visible as a green precipitate. We compared the later to wood which had been treated with solubilised oxine copper but which had been allowed to follow a natural fixation process in which case no discernible precipitation and no discolouration was visible at the surface. This again confirmed our prediction that fixation may be provided at the surface of the substrate by application of solutions which raise the pH of the biocide above the precipitation point in this case 3.3 for oxine copper. Allowing natural diffusion of a formulation into the substrate for example with biocides such as oxine copper also meets a requirement of achieving protection of the substrate without the visible degrade which can occur by the aforementioned photochemical reaction.

We believe that the combination of the specific properties of phosphorous acid wherein the anion has a high hydration energy, and the high levels of this acid in the formulation giving very low pH, combine to produce unusually stable soluble formulations of acid stable biocides. In many instances this combination of high solubility and low pH combine to give a formulation with superior performance when compared to equivalent concentrations of the same biocide in traditional formulations, in certain instances giving synergistic performance for combined biocide formulations.

PCT/NZ95/00029 to The Horticulture and Food Research Institute of New Zealand Limited claims a synergistic combination of phosphorous acid with a triazole. Our work has not been able to confirm this to be so, at least not when triazoles are combined with the biocides of is invention or under the conditions of this invention. The synergism of his prior art may be due to the fact PCT/NZ95/00029 uses neutral salts of phosphorous acid, that is, alkali metal phosphites, not phosphorous acid as generically claimed in said patent. The patent specifically and only demonstrates use of FOLI-R-FOS which is a mixture of mono and di-potassium salts of phosphorous acid. The document thereafter generalises the phosphite ion formed as phosphorous acid. This may mislead the reader to construe the art as phosphorous acid, which is incorrect. These approximately neutral salts will have a pH near 7 and will not solubilise the biocides of this invention in water or polar solvents. Similarly upon review of PCT/NZ95/00029 it is expressed that the formulation is not a solution but preferably a gel and more specifically (claim 6) specifies a suspension. This is not to disclaim the art of said invention for whilst this may be applicable to a living organism such as a tree which is able to translocate the biocides in a systemic fashion, it is not appropriate to logs and lumber or similar products which do not have the facility of systemic translocation. In products of the immediate invention the biocides must be truly solubilised and have a level of stability, that is will not be immediately precipitated by the wood substrate by the increase of pH from the substrate. PCT/NZ95/00029 does not demonstrate solubilisation of the principal biocide nor does it suggest maintaining the pH at a low level during storage or use. More so, the patent indicates a pH around 7, which would be compatible with a living system, not a low pH, as is the target of this invention, which would be toxic to the living system.

Phosphite salts have previously been claimed as biocides in U.S. Pat. No. 5,674,536. These exist as neutral salts.

Similarly U.S. Pat. No. 5,221,791 suggests use of phosphorous acid as the ammonium salt.

Phosphorous acid has been claimed as an effective biocide in the prior art (U.S. Pat. Nos. 4,075,324, 4,119,724 and 4,139,616). These broadly advocate use of phosphorous acid alone or compounds of neutralised phosphorous acid, phosphites, for example, sodium, potassium or ammonium phosphites. This art uses the acid per se as the biocide, not in combination with modern organic biocides, and certainly does not demonstrate use of the phosphorous acid as a solubilising agent for the biocides of this invention.

We explored the effectiveness of phosphorous acid alone to determine whether the enhancement in performance was due the acid itself or to additive effects between the biocides. Our work demonstrated that, whilst phosphorous acid did have fungicidal activity, the results would not explain the high level of performance achieved.

To cite examples, we have clearly demonstrated that metal complexes such as Copper 8-hydroxyquinolinolate solubilised by use of phosphorous acid have a pronounced performance benefit when compared to current art solubilisation of these compounds. Similarly we have demonstrated those biocide combinations of Copper 8-hydroxyquinolinolate, carbendazim (methyl benzimidazoyl carbamate) and fenpropimorph (dimethylethyl phenyl methylpropyl dimethylmorpholine) have superior performance to current art formulations.

For example, a mini disc trial, typically used to assess formulation efficacy, was used to establish relative efficacy of various formulations. Included in the trial were formulations using both phosphoric acid and phosphorous acid.

The following table, Table 4, lists formulation combinations that were developed in initial screening. Compositions in all tables are per cent by weight.

TABLE 4

Prophylactic Compositions

| Example | Phos-phorous Acid | Phos-phoric Acid | Copper 8-hydroxy-quinolinolate | Carben-dazim | Propi-conazole |
|---|---|---|---|---|---|
| 1B |  | 60 | 5 | 5 |  |
| 2B | 60 |  | 5 | 5 |  |
| 3B |  | 60 | 5 | 5 | 2 |
| 4B | 60 |  | 5 | 5 | 2 |
| 5B | 60 |  | 5 |  | 2 |
| 6B | 60 |  |  | 5 |  |

These examples were then diluted in water to produce stable solutions and then tested against a natural fungal inoculum on mini discs of Pinus radiata to determine fungicidal efficacy. The following table, Table 5, illustrates the relative performance of each biocide after 3 weeks in an incubator.

TABLE 5

| Example | Dilution | Efficacy % Control |
|---|---|---|
| 1B | 0.30% | 88 |
| 2B | 0.30% | 100 |
| 3B | 0.30% | 64 |
| 4B | 0.30% | 88 |
| 5B | 0.30% | 76 |
| 6B | 0.30% | 92 |
| Control | 0.30% | 33 |

Control is untreated

This clearly demonstrates that phosphoric acid used in Examples 1B and 3B has inferior performance to otherwise equivalent products such as Examples 2B and 4B. We can also note that Example 3B containing a triazole (propiconazole) is inferior to an otherwise similar product without a triazole, Example 1B. Similarly this inferior performance is demonstrated in the comparison of Examples 4B and 2B.

This work was repeated to confirm the results and extended to include similar biocide combinations to determine whether any enhancement in performance was being achieved. Also phosphorous acid was used in isolation but at similar concentrations to determine relative efficacy.

The formulations used are listed in Table 6.

TABLE 6

Prophylactic Compositions

| Ex-ample | Phos-phorous Acid | 8-hydroxy-quino-linolate Copper | Carben-dazim | Thiaben-dazole | Fenpro-pimorp | Propi-con-zaole |
|---|---|---|---|---|---|---|
| 1C | 60 | 10 | 10 |  |  |  |
| 2C | 60 | 10 |  |  |  | 5 |
| 3C | 60 | 10 |  | 10 |  |  |
| 4C | 60 | 10 |  |  | 5 |  |
| 5C | 60 |  | 10 |  |  |  |
| 6C | 60 |  |  |  |  |  |

These formulations were then diluted and tested using the mini disc method. Also included was an industry standard based on the formulation of U.S. Pat. No. 4,950,685 coded in the trial as KC1 and listed in Table 7.

TABLE 7

| Example | Dilution | Efficacy % Control |
|---|---|---|
| 1C | 0.20% | 100 |
| 2C | 0.20% | 80 |
| 3C | 0.20% | 80 |
| 4C | 0.20% | 100 |
| 5C | 0.20% | 100 |
| 6C | 0.20% | 75 |
| KC1 | 0.20% | 80 |
| Control |  | 60 |

This work demonstrates that the triazole (typically a very expensive biocide) does not produce a cost-effective combination with copper 8-hydroxyquinolinolate compared with carbendazim, thiabendazole and fenpropimorph. It also demonstrates that phosphorous acid alone only gives marginal improvement over the untreated control or specifically, whilst it has some fungicidal activity, it is significantly lower than the formulations of this invention.

Our work then proceeded to determine whether formulations of this invention were superior in efficacy to those demonstrated in U.S. Pat. No. 1,571,814 and NZ Patent 225428 when similar concentrations of active ingredient were applied to the substrate but using the different techniques of each invention. Formulations were prepared accordingly as in Table 8.

TABLE 8

Phophylactic Compositions

| Example | Phos-phorous Acid | Copper 8-hydroxy-quino-linolate | Carben-dazim | DDBSA | Fenpropimorph |
|---|---|---|---|---|---|
| 1D | 60 | 10 | 10 |  |  |
| 2D | 60 | 10 |  |  | 5 |
| 3D | 60 |  | 10 |  |  |
| 4D | 60 |  | 10 |  | 5 |
| 5D | 60 | 10 |  |  |  |
| Com 1 |  | 10 |  | 60 |  |
| Com 2 |  | 10 | 10 | 60 |  |

The formulations were then tested using a mini disc trial with results as disclosed in Table 9.

TABLE 9

| Example | Dilution | Efficacy % Control |
|---|---|---|
| 1D | 0.10% | 95 |
| 1D | 0.20% | 90 |
| 1D | 0.40% | 100 |
| 1D | 0.80% | 100 |
| 2D | 0.10% | 85 |
| 2D | 0.20% | 85 |
| 2D | 0.40% | 100 |
| 2D | 0.80% | 100 |
| 3D | 0.20% | 90 |
| 3D | 0.40% | 100 |
| 3D | 0.80% | 95 |
| 4D | 0.20% | 85 |
| 4D | 0.40% | 95 |
| 4D | 0.80% | 95 |
| 5D | 0.20% | 100 |
| 5D | 0.40% | 90 |
| 5D | 0.80% | 100 |
| Com 1 | 0.30% | 60 |
| Com 1 | 0.60% | 70 |

TABLE 9-continued

| Example | Dilution | Efficacy % Control |
|---|---|---|
| Com 2 | 0.20% | 90 |
| Com 2 | 0.40% | 90 |
| KC1 | 0.20% | 70 |
| KC1 | 0.40% | 55 |
| Control | | 60 |

If we compare Example 1D at 0.1% to Com 2 at 0.2%, a superior performance can be seen at half the biocide concentration, or an enhancement ratio of greater than two in performance. Similarly, this is evident comparing the same two products at 0.4%.

If we compare Example 5D at 0.2% to Com 1 at 0.6% we can see a greater enhancement in performance. This would suggest that the enhancement is a factor of much greater than threefold in this case.

These results clearly demonstrate the improvement in performance achieved by the technology of this invention over that of all the commercial products used (Com 1 (U.S. Pat. No. 1,571,814), Com 2 (NZ 225,428) and KC1 (U.S. Pat. No. 4,950,685)).

Whilst the use of phosphorous acid may impart some benefit to these formulations per se, the data from Tables 4, 5 and 7 indicate that the contribution is not large. We can also compare the enhancement to that claimed, for example, in U.S. Pat. No. 1,571,814 where the preferred acid dodecyl benzene sulphonic acid (DDBSA) has already claims the best enhancement of those acids selected for the invention.

We therefore can interpret these results to indicate a synergism is established for these biocides which relates directly to the method of solubilisation and the physico-chemical properties of the solutions and their interactions with the substrates targeted for the formulations.

It has been stated above that trees are relatively self-protecting whilst alive. Nevertheless some fungal diseases will attack, particularly in times of stress. This may occur during extreme climatic change or if the protective bark is damaged. Methods of treatment are known including application by spray or injection of fungicides. The living tree becomes part of the amelioration process in that the living organism is able to convey the biocide throughout its substrate in a systemic fashion. This ability is lost upon the felling of the tree and the death of its cells. It is also important in use of these systemic fungicides not to add formulating aids which in their own right may be phytotoxic. This necessitates maintenance of pH of a formulation at a moderately neutral level, not too acid or alkaline otherwise the formulation itself can become toxic to the plant.

Since logs, lumber and derivative products are stored in the open they will be exposed to the weather, particularly rain. Since phosphorous acid is completely soluble in water, it will not be an effective biocide alone for this use as it will be eluted or washed from the substrate thus exposing the substrate to fungal degrade. For the applications of this invention it is clearly essential to have a biocide component or components which will remain in or on the substrate to protect the substrate in the case of elution of the phosphorous acid. If it were eluted however, the phosphorous acid does not pose a significant threat to the environment since it is consumed as a mineral source by microorganisms (U.S. Pat. No. 5,327,967).

However, there may in some instances be a need for the user to fix or precipitate the biocides at the surface or to ensure that once inside the substrate that the biocides are prevented from eluting from the surface. The technology of this invention allows convenient control of this process in that subsequent to application of the biocide formulation which is at low pH, a subsequent application of a second formulation which raises the pH will then precipitate or fix the biocides and prevent their movement. This second treatment may be another biocide formulation of higher pH or may be a formulation of higher pH without biocidal properties. An essential feature of the second formulation is that it must raise the pH to approximately 3.5 or above, This may require adjustment on a case by case basis because it will depend on the strength of original treating solution applied. It could also easily be controlled by a strongly buffering formulation with the correct pH, for example, one could apply mono sodium or mono potassium salts of phosphoric acid or phosphorous acid in which case the pH will be approximately 4. The latter would provide the benefit of additional biocidal action. This process can be applied to formulations of low pH not necessarily produced by the methods of this invention for example, those of NZ Patent 225428 and U.S. Pat. No. 1,571,814.

The following comments also apply to a preferred embodiment of NZ 225,428 and U.S. Pat. No. 1,571,814;

highly polar aprotic solvents are expensive dodecylbenzenesulphonic acid is expensive dodecylbenzenesulphonic has a high level of toxicity.

dodecylbenzenesulphonic acid is the precursor for a surfactant and causes excessive foaming when this formulation is mixed with water and used.

the formulation has an odour which is disliked the product becomes viscous and almost solid at low temperatures the pH is not stable.

in contact with wood, sawdust or wood extractives the biocides precipitate prematurely and are lost from solution which causes waste of biocide The product of this invention is novel in that;

it eliminates the expensive highly polar aprotic solvent it contains no relatively toxic dodecylbenzenesulphonic acid it does not cause foaming it has no odour it is very fluid even at low temperatures it provides significantly higher biological performance at equivalent biocide concentrations to the above invention the pH is stable and biocides remain in solution when exposed to wood, sawdust or wood extractives Referring to aforementioned PCT/NZ95/00029, we wished to determine whether organic biocides of the present invention would remain in solution at the preferred pH of the present invention and would subsequently precipitate as the pH increased subsequent to application.

As an example, we added fenpropimorph to water and found it would not dissolve. The dispersion had a pH of approximately 7.0. We decreased the pH by addition of phosphorous acid. Considerable acid was required before complete dissolution occurred and it was found that at the concentration of biocide preferred that the pH needed to be well below 4.0 and preferably below 3.0.

We compared our findings with information from the manufacturer of fenpropimorph who has provided the solubility data in water in Table 10.

TABLE 10

| pH | Solubility (mg/l) |
|---|---|
| 9–11 | 3.5 |
| 7 | 4.3 |
| 4.4 | 7300 |

We have achieved solubility of fenpropimorph of as much as 10% by weight. This high level of solubility remains when that active is also the presence of 10–20% of other biocides.

We have studied NZ 264671 wherein it is claimed phenylbenzamide compounds form synergistic mixtures when combined with fungicides including one or more of the group comprising maneb, mancozeb, folpet, a copper compound, phosethyl-Al, phosphorous acid or one of its salts, chlorothalonil, fluazinam amongst others.

In the embodiments the formulation types include emulsifiable concentrates, suspension concentrates, wettable powders and granules.

This prior art nowhere describes highly concentrated solutions of biocides in phosphorous acid and polar solvents.

This may be ascribed to the fact that the secondary fungicides may not be stable in combination. For example it is known to those versed in the art that maneb, mancozeb and phosethyl-Al are all decomposed by acids (including phosphorous acid) and that folpet is decomposed by water. Therefore in NZ 264671 the combination of phenylbenzamide, phosphorous acid and one or more of maneb, mancozeb, phosethyl-Al and/or folpet can not be viable. Therefore the broad claims of NZ 264671 are a nonsense.

Similarly, since for example, one of the target species of NZ 264671 is *Vitis vinifera* or grape seedlings and cuttings, the composition disclosed can not be acidic, and particularly acidic to a pH below 4.0. Otherwise all the plants to which the composition is being applied will die before any of the desired results can be achieved.

The present invention is clearly very different from that of the invention disclosed in NZ 264671.

The products of the present invention outperform products of NZ 225,428, U.S. Pat. No. 4,950,685 and U.S. Pat. No. 1,571,814. It is also believed that there is synergism between the biocides.

EXAMPLE 1

Phosphorous acid 60 parts, oxine copper 10 parts, water 30 parts, are combined to provide a stable transparent solution.

EXAMPLE 2

Phosphorous acid 60 parts, oxine copper 10 parts, carbendazim 10 parts, water 20 parts, are combined to provide a stable transparent solution.

EXAMPLE 3

Phosphorous acid 60 parts, oxine copper 10 parts, thiabendazole 10 parts, water 20 parts, are combined to provide a stable transparent solution.

EXAMPLE 4

Phosphorous acid 60 parts, oxine copper 10 parts, propiconazole 5 parts, water 30 parts, are combined to provide a stable transparent solution.

EXAMPLE 5

Phosphorous acid 60 parts, oxine copper 10 parts, fenpropimorph 5 parts, water 30 parts, are combined to provide a stable transparent solution.

EXAMPLE 6

Phosphorous acid 30 parts, oxine copper 10 parts, water 10 parts, are combined to provide a stable transparent solution containing more than 500 grams per litre of oxine copper.

EXAMPLE 7

Phosphorous acid 12 parts, fenpropimorph 2 parts, water 26 parts, are combined to provide a stable transparent solution.

EXAMPLE 8

Phosphorous acid 16 parts, oxine copper 4 parts, urea 4 parts, water 16 parts, are combined to provide a stable transparent solution.

EXAMPLE 9

Phosphorous acid 4 parts, carbendazim 1 parts, water 5 parts, are combined to provide a stable transparent solution.

EXAMPLE 10

Phosphorous acid 5 parts, carbendazim 1 part, fenpropimorph 0.5 parts, water 3.5 parts, are combined to provide a stable transparent solution.

EXAMPLE 11

Phosphorous acid 4 parts, cupric hydroxide 0.6 parts, water 5.4 parts, are combined to provide a stable transparent solution.

EXAMPLE 12

Phosphorous acid 4 parts, benzalkonium chloride 1 part, water 5.4 parts, are combined to provide a stable transparent solution.

EXAMPLE 13

Phosphorous acid 64 parts, carbendazim 11 parts, propiconazole 4.5 parts, water 22 parts, are combined to provide a stable transparent solution.

EXAMPLE 14

Phosphorous acid 60 parts, carbendazim 10 parts, oxine copper 10 parts, propiconazole 4 parts, water 20 parts, are combined to provide a stable transparent solution.

EXAMPLE 15

Oxine copper 100 gm of oxine copper is dissolved in 480 gm phosphorous acid plus 655 grams of water to give 1235 grams of transparent green solution with a density of approximately 1.24 and containing 100 grams per litre of oxine copper.

EXAMPLE 16

Oxine copper plus Carbendazim 100 grams oxine copper plus 100 grams of Carbendazim is dissolved in 700 grams phosphorous acid plus 453 grams of water to give 1353 grams of transparent green solution with density approximately 1.34 and containing 100 grams per litre each of oxine copper and Carbendazim.

EXAMPLE 17

Oxine copper plus Fenpropimorph 100 grams of oxine copper plus 50 grams of Fenpropimorph is dissolved in 500 grains of phosphorous acid plus 598 grams of water to give 1248 grams of transparent green solution with density of approximately 1.25 containing 100 grams of oxine copper per litre plus 50 grams of Fenpropimorph per litre.

Frequently additional biocides are included in formulations to extend performance or more specifically to target specific fungal problems. Having produced the basic formulation other biocides may be added. This possibility is also the case for this invention with the proviso that the biocides are stable in acid conditions. By reference we include those which are listed, for example, in U.S. Pat. No. 1,571,814 such as cis-N-(trichloromethyl)thio 4-cyclohexane-1,2-dicarboxamide, diiodomethyl-para-tolyl sulphone, 2-n-octyl-4-isothiazolin-3-one, 2-benzisothiazolin-3-one, 8-hydroxyquinoline however this list is not exhaustive, other acid stable biocides may be included. Similarly, insecticides can at times be included with the same proviso. These may include but is not restricted to organo chlorine and organophoshate insecticides, In certain circumstances application of viscosity enhancing agents may provide additional benefits. For example, when a user may wish to apply a heavier loading to the substrate which might not otherwise be achieved with an unmodified solution, in which case increasing the viscosity with a thickening agent will achieve the desired result. The thickening agent will necessarily need to be effective at low pH.

The present invention by full solubilisation of preferred biocides provides a formulation which;

reduces or eliminates foaming, reduces or eliminates premature precipitation of biocides enhances penetration of biocides into the substrate by maintaining solubility improves application properties by eliminating precipitation and thereby enhancing solution rheology eliminates organic adjuvants which would otherwise be used thereby reducing the biological load on the environment reduces cost by eliminating expensive adjuvants reduces worker and environment impact by eliminating potentially toxic adjuvants.

We believe this invention to be novel and to offer the user an alternative with significant benefits.

A key feature in the protection of solid wood products, for example, logs is the need to treat at some depth from the wood surface. Traditional products are unable to fulfill this role. Testing to compare products of this invention demonstrates that these novel formulations can achieve the required performance.

Table 11 illustrates the performance of products of this invention compared to products containing the same base biocide yet using traditional formulating techniques as follows:

TABLE 11

| | |
|---|---|
| BioControl | test using biological control with a competing fungus species. |
| DDAC/IPBC | a fungicide combination common in industry |
| Exptl | an experimental biocide similar to DDAC/IPBC Formulation |

TABLE 11-continued

| | |
|---|---|
| Trad 1 | oxine copper solubilised with dodecyl/benzenesulphonic acid* |
| Tech 1 | oxine copper solubilised using the invention (Example 2D of Table 8) |
| Tech 2 | oxine copper solubilised using the invention (Example 5D of Table 8) |
| Trad 2 | oxine copper solubilised with dodecylbenzenesulphonic acid* |
| Trad 3 | oxine copper solubilised with dodecylbenzenesulphonic acid* |
| Control | untreated control material |

*U.S. Pat. No. 1,571,814

It should be noted that in this trial that the concentration of oxine copper used in Trad 1, 2, and 3 and in the Tech 1 and 2 formulations of the present invention are the same. Please see enclosed FIG. 1 which depicts the outcomes. If one compares the performance of Tech 1 and 2 with Trad 1, 2 and 3 at log age 3 (z-axis) a considerable and consistent enhancement in performance can be seen.

We have previously demonstrated that although phosphorous acid has a slight but ineffective level of fungicidal activity, in this study we have demonstrated a significant level of synergism using the combination of this invention. Further because the user expects a level of control remote from the wood surface, ie; within the log substrate, products of this invention have not only provided the increase in performance desired but also have achieved the performance at depth, unlike the traditional biocides which only provide protection of the wood surface.

Preferably forms the present invention will now be described with reference to the accompanying figures in which:

FIG. 1 illustrates the performances of products of the present invention against products containing the same base biocide using other formulating techniques.

What is claimed is:

1. A biocidal composition being in the form of:
  (i) a solution carried by water, or
  (ii) as a solids mix soluble in water
  said composition consisting essentially of:
    phosphorous acid; and,
    at least one biocide selected from the group consisting of benzimidazoles, precursors of benzimidazoles, substituted morpholines, organic chelate complexes of metals, precursors of organic chelate complexes of metals, and metal ions selected from the group consisting of Al, Co, Cu, Mn, Mo, Ni, W, V, and Zn wherein as a solution in the presence of water, pH is or below 4, and wherein the phosphorus acid is present in the composition in stoichiometric excess of the at least one biocide.

2. The composition of claim 1, wherein said composition is an antibacterial composition or an antifungal composition.

3. The composition of claim 1, wherein said at least one biocide is stable at a pH below 4 or said biocide or biocide precursors form or become stable biocides as the pH of the use strength solution rises to a pH of 4.

4. The composition of claim 1, wherein the pH is or will be below 3.

5. The composition of claim 4, wherein the pH is or will be below 2.5.

6. The composition of claim 1, wherein said biocide is benzimidazole.

7. The composition of claim 1, wherein said biocide is said organic chelate complex of a metal.

8. The composition of claim 7, wherein said biocide is the organic chelate complex of an 8-hydroxyquinoline.

9. The composition of claim 7, wherein the metal is copper or zinc and the complex is an oxine of copper or zinc cations with 8-hydroxyquinoline.

10. The composition of claim 9, wherein said cations are copper cations.

11. The composition of claim 1, wherein said composition consists essentially of a stable highly concentrated solution of biocide.

12. The composition of claim 11, wherein said biocide is a metal chelate or the precursors thereof.

13. The composition of claim 12, wherein said metal chelate is a metal chelate of oxine or a mixed chelate thereof or the precursors thereof.

14. The composition of claim 13, wherein said metal chelate is oxine copper or the precursors thereof.

15. The composition of claim 1, wherein said at least one biocide is acid stable.

16. An antifungal composition in the form of a solution consisting essentially of:
oxine copper;
phosphorous acid; and,
water,
wherein pH is less than 4, and
wherein the phosphorous acid is present in stoichiometric excess of the oxine copper.

17. A biocidal composition consisting essentially of:
phosphorous acid;
at least one biocide chosen from the group consisting of benzimidazoles,
precursors of benzimidazoles, substituted morpholines, organic chelate complexes of metals, precursors of organic chelate complexes of metals, metal ions selected from the group consisting of Al, Co, Cu, Mn, Mo, Ni, W, V, and Zn;
water; and
an additional hydrogen ion source; and,
wherein said composition has a pH less than 4, and
wherein the phosphorous acid is present in stoichiometric excess of the at least one biocide.

18. A biocidal composition consisting essentially of:
phosphorous acid;
at least one biocide chosen from the group consisting of benzimidazoles,
precursors of benzimidazoles, substituted morpholines, organic chelate complexes of metals, precursors of organic chelate complexes of metals, metal ions selected from the group consisting of Al, Co, Cu, Mn, Mo, Ni, W, V, and Zn;
water; and,
an insecticide; and,
wherein said composition has a pH less than 4, and
wherein the phosphorous acid is present in stoichiometric excess of the at least one biocide.

19. A biocidal composition consisting essentially of:
phosphorous acid;
at least one biocide chosen from the group consisting of benzimidazoles, precursors of benzimidazoles, substituted morpholines, organic chelate complexes of metals, precursors of organic chelate complexes of metals, metal ions selected from the group consisting of Al, Co, Cu, Mn, Mo, Ni, W, V, and Zn;
water; and,
a viscosity enhancer; and,
wherein said composition has a pH less than 4, and
wherein the phosphorous acid is present in stoichiometric excess of the at least one biocide.

20. A biocidal composition consisting essentially of:
phosphorous acid;
at least one biocide chosen from the group consisting of benzimidazoles, precursors of benzimidazoles, substituted morpholines, organic chelate complexes of metals, precursors of organic chelate complexes of metals, metal ions selected from the group consisting of Al, Co, Cu, Mn, Mo, Ni W, V, and Zn;
water; and,
a latent buffer which will raise the pH of the solution over time to facilitate fixing of the biocide to a substrate upon use; and,
wherein said composition has a pH less than 4, and
wherein the phosphorous acid is present in stoichiometric excess of the at least one biocide.

21. The biocidal composition of claim 20, wherein said latent buffer is urea.

22. A method of forming a biocidal composition (i) being in or to be in the form of a solution carried by water or (ii) as a solids mix soluble in water, said composition consisting essentially of:
phosphorous acid; and,
at least one biocide chosen from the group consisting of benzimidazoles, precursors of benzimidazoles, substituted morpholines, organic chelate complexes of metals, precursors of organic chelate complexes of metals, metal ions selected from the group consisting of Al, Co, Cu, Mn, Mo, Ni, W, V, and Zn,
wherein, as a solution, in the presence of water, pH is below 4, said method comprising any one of the following
(1) admixing the individual composition components to provide dissolution to produce the solution;
(2) adding to the biocide precursors with remaining composition components to form the solution;
(3) admixing the components and then adding water to form the solution;
(4) adding to the biocide precursors with remaining components and then adding water to form the solution;
(5) admixing the individual composition components to form the solution and then adding further biocide components; and
(6) admixing the individual composition components and then adding a source of hydrogen ions to reduce the pH of the composition to below 4 to form the solution.

23. A method of treating a substrate comprising at least the step of applying to the substrate an effective amount of a composition selected from the group consisting of:
(a) a biocidal composition consisting essentially of phosphorous acid and at least one biocide selected from the group consisting of benzimidazoles, precursors of benzimidazoles, substituted morpholines, organic chelate complexes of metals, precursors of organic chelate complexes of metals, and metal ions selected from the group consisting of Al, Co, Cu, Mn, Mo, Ni, W, V, and Zn wherein as a solution in the presence of water, pH is or below 4 and wherein the phosphorus acid is present in the composition in stoichiometric excess of the at least one biocide;

(b) an antifungal composition in the form of a solution consisting essentially of oxine copper; phosphorous acid; and water, wherein pH is less than 4, and wherein the phosphorous acid is present in stoichiometric excess of the oxine copper;

(c) a biocidal composition consisting essentially of phosphorous acid; at least one biocide chosen from the group consisting of benzimidazoles, precursors of benzimidazoles, substituted morpholines, organic chelate complexes of metals, precursors of organic chelate complexes of metals, metal ions selected from the group consisting of Al, Co, Cu, Mn, Mo, Ni, W, V, and Zn; water; and an additional hydrogen ion source; and, wherein said composition has a pH less than 4, and wherein the phosphorous acid is present in stoichiometric excess of the at least one biocide;

(d) a biocidal composition consisting essentially of phosphorous acid; at least one biocide chosen from the group consisting of benzimidazoles, precursors of benzimidazoles, substituted morpholines, organic chelate complexes of metals, precursors of organic chelate complexes of metals, metal ions selected from the group consisting of Al, Co, Cu, Mn, Mo, Ni, W, V, and Zn; water; and, an insecticide; and, wherein said composition has a pH less than 4, and wherein the phosphorous acid is present in stoichiometric excess of the at least one biocide;

(e) a biocidal composition consisting essentially of phosphorous acid; at least one biocide chosen from the group consisting of benzimidazoles, precursors of benzimidazoles, substituted morpholines, organic chelate complexes of metals, precursors of organic chelate complexes of metals, metal ions selected from the group consisting of Al, Co, Cu, Mn, Mo, Nl, W, V, and Zn; water; and, a viscosity enhancer; and, wherein said composition has a pH less than 4, and wherein the phosphorous acid is present in stoichiometric excess of the at least one biocide; and (f) a biocidal composition consisting essentially of phosphorous acid; at least one biocide chosen from the group consisting of benzimidazoles, precursors of benzimidazoles, substituted morpholines, organic chelate complexes of metals, precursors of organic chelate complexes of metals, metal ions selected from the group consisting of Al, Co, Cu, Mn, Mo, Ni W, V, and Zn; water; and, a latent buffer which will raise the pH of the solution over time to facilitate fixing of the biocide to a substrate upon use; and, wherein said composition has a pH less than 4, and wherein the phosphorous acid is present in stoichiometric excess of the at least one biocide.

24. The method of claim 23, wherein said substrate has a pH above the composition.

25. The method of claim 23, wherein the substrate is wood.

26. The method of claim 23, wherein the method is for wood preservation.

27. The method of claim 23, which further comprises applying an additional biocidal composition to said substrate.

28. The method of claim 23, which further comprises applying to said substrate a pH increasing solution to facilitate the fixing of the biocides following the application of the biocidal composition to said substrate.

29. The biocidal composition of claim 1, wherein the solution contain greater than 10% biocide by weight.

30. A biocidal composition being a solution and having a pH of below 4, the composition consisting essentially of:

at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni W, V and Zn;

phosphite ions;

a hydrogen ion source; and water; and wherein the phosphite ions are present in stoichiometric excess of the at least one biocide.

31. The biocidal composition of claim 30, wherein a phosphite salt is the source of phosphite ions.

32. The biocidal composition of claim 30, wherein phosphorous acid is the source of phosphite ions.

33. The biocidal composition of claim 30, wherein phosphorous acid is the source of phosphite ions and hydrogen ions.

34. A biocidal composition being a solution and having a pH of below 4, the composition consisting essentially of:

at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn;

phosphite ions;

a hydrogen ion source;

an insecticide;

water; and wherein the phosphite ions are present in stoichiometric excess of the at least one biocide.

35. A biocidal composition being a solution and having a pH of below 4, the composition consisting essentially of:

at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn;

phosphite ions;

a hydrogen ion source;

a viscosity enhances;

water; and wherein the phosphite ions are present in stoichiometric excess of the at least one biocide.

36. A biocidal composition being a solution and having a pH of below 4, the composition consisting essentially of:

at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn;

phosphite ions;

a hydrogen ion source;

a latent buffer which will raise the pH of the composition over time to facilitate fixing of the biocide to a substrate upon use;

water; and wherein the phosphite ions are present in stoichiometric excess of the at least one biocide.

37. The biocidal composition of claim 31, wherein the biocide is greater than 10% by weight.

38. A biocidal composition being in the form of a solids mix soluble in water to form a solution having a pH of below 4, said composition consisting essentially of:
- at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn;
- a hydrogen ion source; and
- a compound capable of releasing phosphite ions when in the solution; and
- wherein the phosphite ions are in stoichiometric excess of the at least one biocide in the solution.

39. A method of treating a substrate comprising at least the step of applying to such substrate an effective amount of a biocidal composition selected from the group consisting of
- (a) a biocidal composition being a solution and having a pH of below 4, the composition consisting essentially of:
  - at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn;
  - phosphite ions;
  - a hydrogen ion source; and
  - water; and wherein the phosphite ions are present in stoichiometric excess of the at least one biocide;
- (b) a biocidal composition being a solution and having a pH of below 4, the composition consisting essentially of:
  - at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn;
  - phosphate ions;
  - a hydrogen ion source;
  - an insecticide;
  - water; and wherein the phosphite ions are present in stoichiometric excess of the at least one biocide;
- (c) a biocidal composition being a solution and having a pH of below 4, the composition consisting essentially of:
  - at least one biocide chosen from the group consistin of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn;
  - phosphite ions;
  - a hydrogen ion source;
  - a viscosity enhancer;
  - water; and wherein the phosphite ions are present in stoichiometric excess of the at least one biocide;
- (d) a biocidal composition being a solution and having a pH of below 4, the composition consistin essentially of:
  - at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn;
  - phosphite ions;
  - a hydrogen ion source;
  - a latent buffer which will raise the pH of the composition over time to facilitate fixing of the biocide to a substrate upon use;
  - water; and wherein the phosphite ions are present in stoichiometric excess of the at least one biocide; and
- (e) a biocidal composition being in the form of a solids mix soluble in water to form a solution having a pH of below 4, said composition consisting essentially of:
  - at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn;
  - a hydrogen ion source; and
  - a compound capable of releasing phosphite ions when in the solution; and wherein the phosphite ions are in stoichiometric excess of the at least one biocide in the solution.

40. A method of treating a substrate comprising at least the step of applying to such substrate an effective amount of a biocidal composition in accordance with claim 5.

41. A method of forming a biocidal composition (i) being in or to be hit the form of a solution carried by water or (ii) as a solids mix soluble in water, said composition consisting essentially of:
- at least one phosphite compound capable of releasing phosphite ions at a pH of below 4;
- at least one biocide chosen from the group consisting of benzimidazoles, precursors of benzimidazoles, substituted morpholines, organic chelate complexes of metals, precursors of such organic complexes of metals, metal ions selected from the group consisting of Al, Co, Cu, Mn, Mo, Ni, W, V and Zn; and,
- a hydrogen ion source; and,
- wherein, as a solution, in the presence of water, the pH is below 4,
- said method comprising any one of the following:
  - (1) admixture of the individual composition components and mixing to provide dissolution to produce the solution;
  - (2) addition of biocide precursors with remaining composition components to form the solution;
  - (3) admixture of components prior to addition of water with subsequent addition of water to form the solution;
  - (4) addition of biocide precursors with remaining components prior to addition of water with subsequent addition of water to form the solution,
  - (5) admixture of the individual composition components and mixing to form the solution with subsequence addition of further biocide components, or
  - (6) admixture of the individual composition components with subsequent addition of a source of hydrogen ions.

* * * * *